United States Patent [19]
DeWindt et al.

[11] Patent Number: 6,146,371
[45] Date of Patent: *Nov. 14, 2000

[54] OVAL-SHAPED CARDIAC CANNULA

[75] Inventors: David B. DeWindt, Grand Rapids; Ronald A. DeVries, Zeeland, both of Mich.; Steven M. Gundry, Redlands, Calif.; William E. Sidor, Rockford, Mich.

[73] Assignee: Medtronic, Inc., Minneapolis, Minn.

[ * ] Notice: This patent is subject to a terminal disclaimer.

[21] Appl. No.: 09/131,579

[22] Filed: Aug. 10, 1998

Related U.S. Application Data

[63] Continuation of application No. 08/780,995, Jan. 9, 1997, Pat. No. 5,817,071.

[51] Int. Cl.⁷ .................................................. A61M 31/00
[52] U.S. Cl. ...................... 604/506; 604/264; 604/164
[58] Field of Search .......................... 604/500, 506–508, 604/104, 158, 164, 167, 169, 264, 523

[56] References Cited

U.S. PATENT DOCUMENTS

| | | | |
|---|---|---|---|
| 3,734,083 | 5/1973 | Kolin | 604/104 |
| 4,129,129 | 12/1978 | Amrine | 604/500 |
| 4,350,161 | 9/1982 | Davis, Jr. . | |
| 4,451,252 | 5/1984 | Martin . | |
| 4,543,087 | 9/1985 | Sommercorn et al. . | |
| 4,596,548 | 6/1986 | DeVries et al. . | |
| 4,619,643 | 10/1986 | Bai . | |
| 4,639,252 | 1/1987 | Kelly et al. . | |
| 4,675,004 | 6/1987 | Hadford et al. . | |
| 4,784,651 | 11/1988 | Hickey . | |
| 4,795,439 | 1/1989 | Guest | 604/264 |
| 4,804,359 | 2/1989 | Grunwald et al. | 604/4 |
| 4,808,158 | 2/1989 | Kreuzer et al. | 604/49 |
| 4,846,806 | 7/1989 | Wigness et al. | 604/256 |
| 5,045,075 | 9/1991 | Ersek . | |
| 5,160,325 | 11/1992 | Nichols et al. | 604/523 |
| 5,180,387 | 1/1993 | Ghajar et al. . | |
| 5,201,712 | 4/1993 | Bryant | 604/164 |
| 5,333,614 | 8/1994 | Feiring . | |
| 5,348,536 | 9/1994 | Young et al. . | |
| 5,374,245 | 12/1994 | Mahurkar . | |
| 5,451,206 | 9/1995 | Young . | |
| 5,536,251 | 7/1996 | Evard et al. . | |
| 5,554,136 | 9/1996 | Luther | 604/264 |
| 5,556,390 | 9/1996 | Hicks | 604/523 |
| 5,569,182 | 10/1996 | Twardowski et al. . | |
| 5,762,629 | 6/1998 | Kambin . | |
| 5,817,071 | 10/1998 | DeWindt et al. | 604/264 |

FOREIGN PATENT DOCUMENTS 2172203A  9/1986  United Kingdom .

OTHER PUBLICATIONS

Arom et al.; Mini–Sternotomy for Coronary Artery Bypass Grafting; Ann. Thorac. Surg. 1996; 61: 1271–2.
Acuff et al.; Minimally Invasive Coronary Artery Bypass Grafting; Ann. Thorac. Surg. 1996; 61: 135–7.
Mathias; Keyhole Cardiac Surgery, MIS Techniques Could Transform Heart Surgery; OR Manager, Jul. 1996, vol. 12, No. 7.
PCT Form/ISA/220, International Search Report for Application PCT/US 98/00361; Jun. 12, 1998.

Primary Examiner—Wynn Wood Coggins
Assistant Examiner—Jennifer R. Sadula
Attorney, Agent, or Firm—Foley & Lardner

[57] ABSTRACT

A cannula comprises a proximal end, a distal end, and a lumen extending between the proximal and distal ends, wherein at least a portion of the cannula body is non-circular in cross section, preferably oval. A cannula wherein a portion of the cannula body is oval in cross section is ideally suited in surgical procedures wherein the cannula extends through a percutaneous aperture. The oval portion of the cannula body utilizes the space of the percutaneous aperture efficiently, thereby minimizing the necessary size of the access aperture.

17 Claims, 4 Drawing Sheets

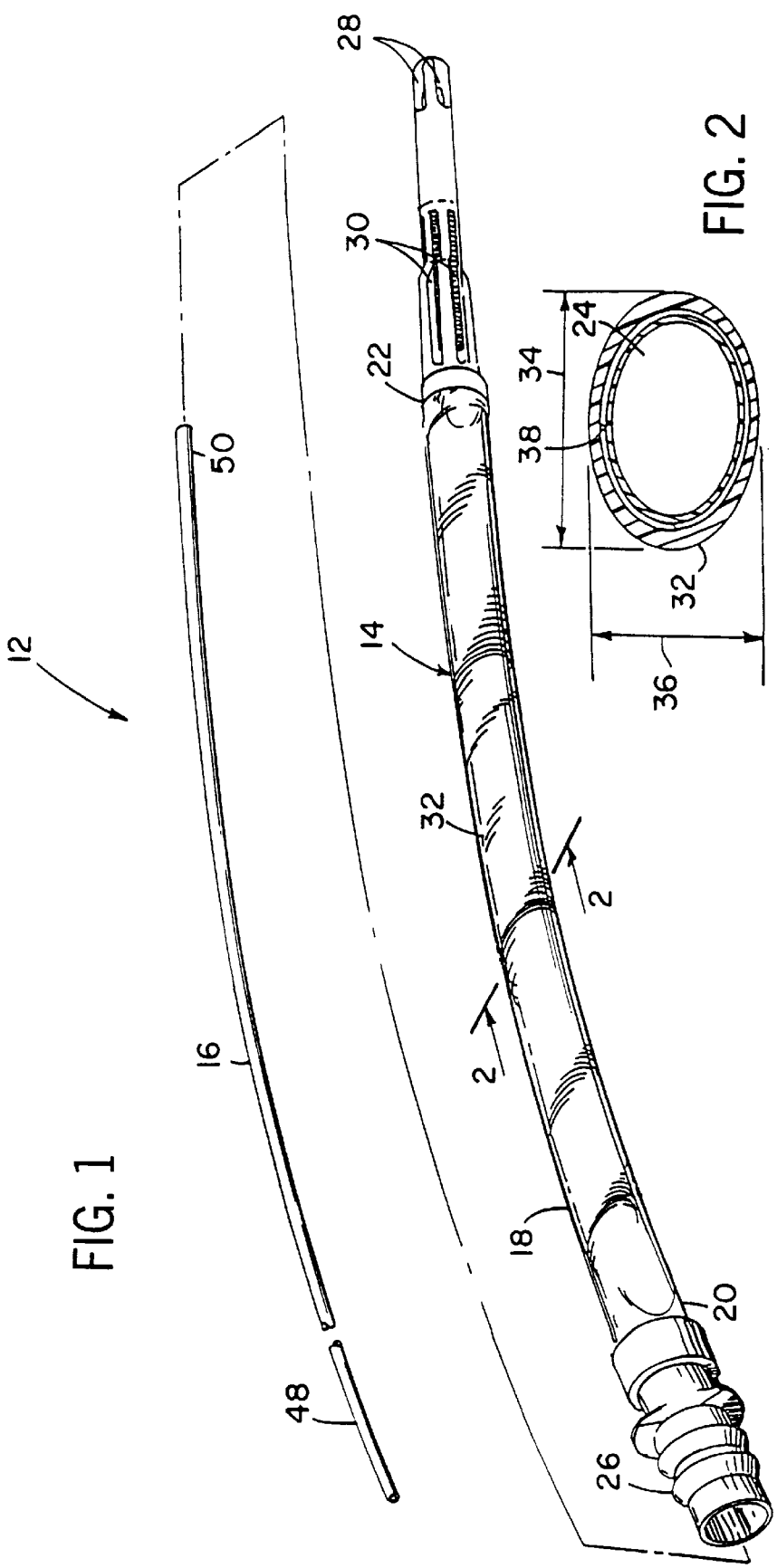

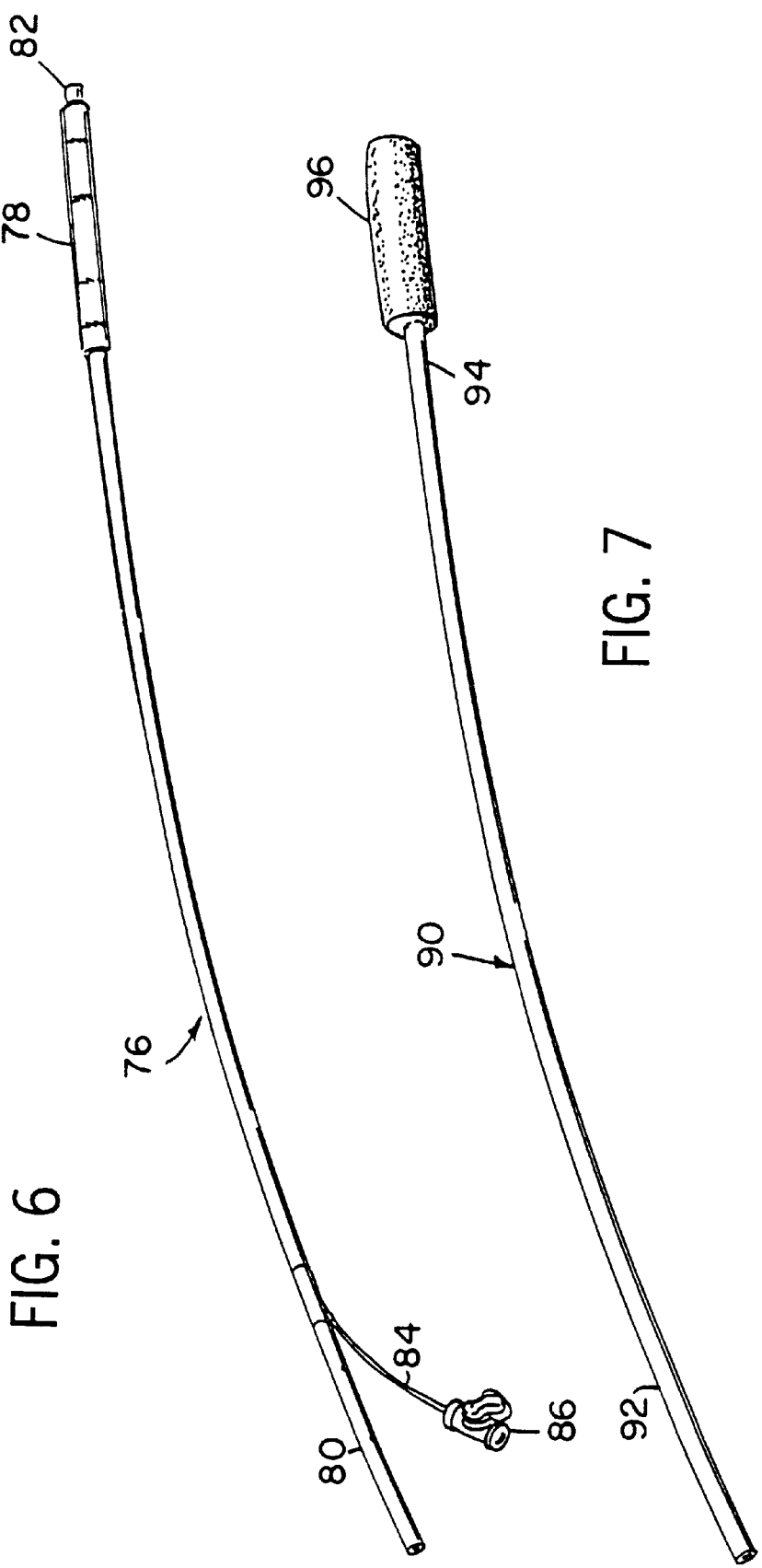

6,146,371

OVAL-SHAPED CARDIAC CANNULA

This is a continuation of Ser. No. 08/780,925 is now U.S. Pat. No. 5,817,071 filed Jan. 9, 1997.

BACKGROUND OF THE INVENTION

1. Field of the Invention

This invention relates to cannulas and, more particularly, to a cannula which is oval-shaped in cross section and therefore ideally suited for use in minimally invasive surgical procedures.

2. Description of the Related Art

Cannulas have a wide variety of applications during surgical procedures. For example, in coronary surgery, venous and arterial cannulas are used to conduct blood between the body and bypass equipment. Cannulas are used to conduct cardioplegia solution for both antigrade and retrograde solution administration, and cannulas are also used as vents, sumps, and for chest tube fluid suction. The structure for these known cannulas generally comprises a cannula body which is circular in cross section and has at least one lumen extending therethrough which is similarly circular in cross section. Examples of these structures are seen in U.S. Pat. Nos. 4,639,252; 4,129,129; and 5,395,330.

A recent trend in surgical procedures is to minimize the size of the access apertures formed in the chest cavity. These procedures include mini-sternomoty and minimally invasive cardiac surgery. In each of these procedures, the goal is to reduce the size of the aperture in the chest wall. One problem in achieving this goal is the size, geometry, and space requirements for the instruments, cannulas, and the like which must pass through the reduced size apertures.

SUMMARY OF THE INVENTION

The cannula according to the invention overcomes the problems of the prior art by providing a cannula having a prescribed geometry which more efficiently occupies the space of the aperture without adversely affecting the fluid flow rate therethrough.

In a first aspect, the invention comprises a cannula used in conducting fluid to or from the body. The cannula has a cannula body with a proximal end, a distal end, and a lumen extending between the two ends. A fluid outlet is formed on the proximal end and at least one fluid inlet is formed adjacent the distal end. The cross section of a first portion of the cannula body is non-circular, preferably oval. The non-circular portion has a major cross-sectional axis and a minor cross-sectional axis wherein the length of the major axis is greater than the length of the minor axis.

In another embodiment, the cannula body also includes a second non-circular portion which is also preferably oval in cross section. Preferably, the major axis of the first oval portion is parallel to the minor axis of the second oval portion.

In another embodiment, an obturator is telescopically received in the lumen of the cannula and the obturator effectively seals at least a portion of the fluid inlet when the obturator is fully received in the cannula lumen. Preferably, the obturator includes some form of sealing means which are adapted to pass through the non-circular portions of the cannula and also seal the fluid inlets. In one embodiment, the sealing means comprises an expandable balloon. In another embodiment, the sealing means comprises a pliable foam member.

The invention is also directed to a method of positioning a fluid conducting cannula in a body. The method comprises the steps of providing a cannula such as that described above and providing a percutaneous aperture in the body. The distal end of the cannula is inserted into the body through the percutaneous aperture, and the cannula is positioned so that the oval portion of the cannula extends through the percutaneous aperture. In this position, the oval portion of the cannula body utilizes the available cross-sectional area of the access aperture more efficiently than a traditional round cannula.

BRIEF DESCRIPTION OF THE DRAWINGS

The invention will now be described with reference to the drawings in which:

FIG. 1 is a perspective view of a venous cannula assembly wherein at least a portion of the cannula body is oval in cross section;

FIG. 2 is a cross section taken along the lines 2—2 of FIG. 1 showing the oval cross section of the cannula body;

FIG. 6 is a plan view of a second embodiment of the obturator for the cannula assembly; and FIG. 7 is a plan view of a third embodiment of the obturator.

DETAILED DESCRIPTION OF THE PREFERRED EMBODIMENTS

Figure 3:
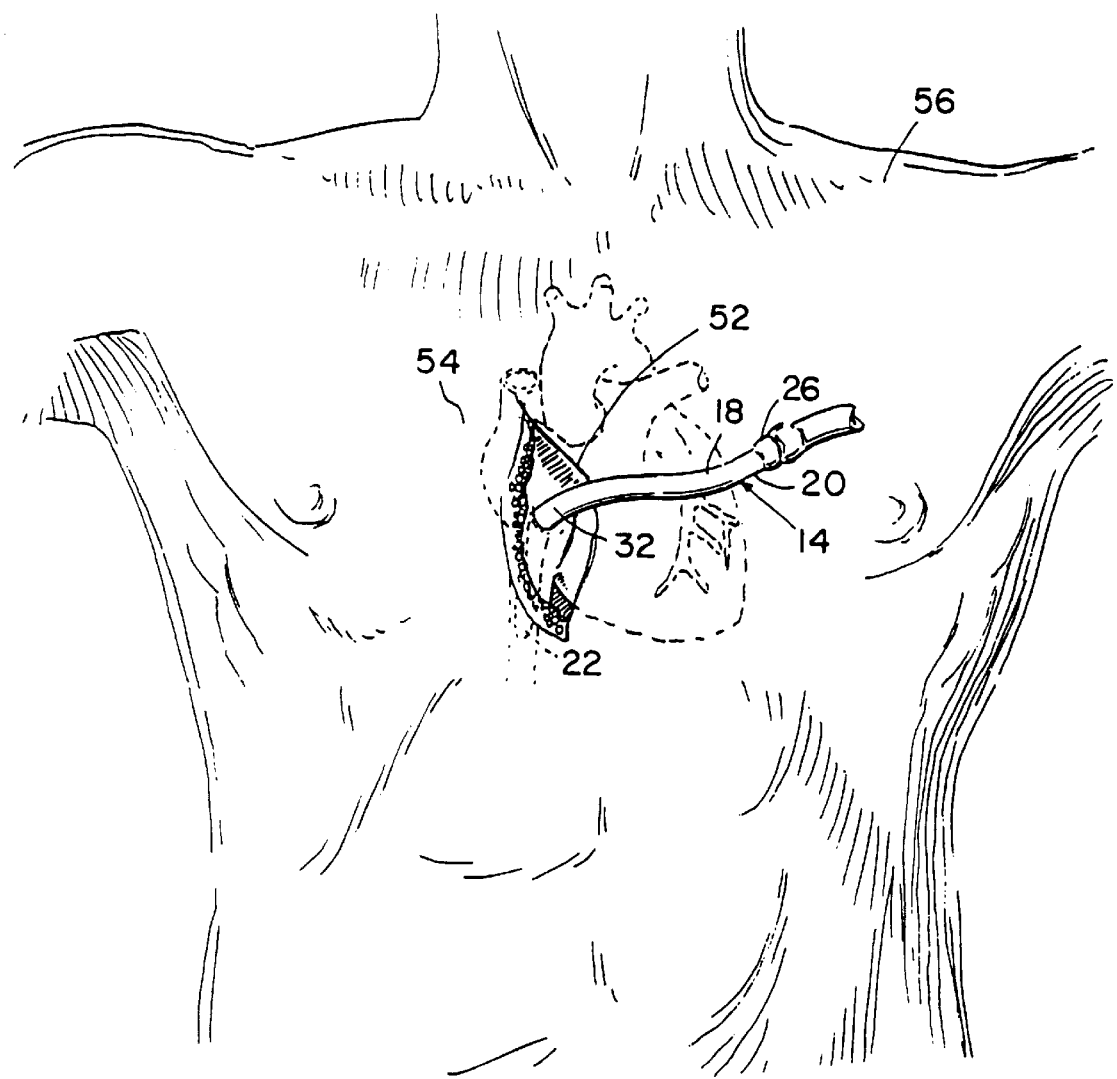
FIG. 3 is a plan view of a patient showing a cannula according to the invention passing through a mini-thoracotomy.

Turning now to the drawings and to FIGS. 1 and 2 in particular, a first embodiment of the cannula assembly according to invention is shown. The first embodiment of the cannula assembly 12 comprises a cannula 14 and an obturator 16 which is selectively, telescopically received in the cannula 14. The cannula 14 comprises a cannula body 18 having a proximal end 20, a distal end 22, and a lumen 24 extending between the proximal and distal ends. A conventional luer connector 26 is preferably provided on the proximal end 20, and the distal end 22 preferably includes at least one fluid inlet aperture for the receipt of fluid into the lumen. A helically wound reinforcing spring 38 is preferably, integrally formed into the cannula body 18. The cannula seen in FIGS. 1 and 2 includes a first set of fluid apertures 28 formed immediately adjacent the distal end 22 and a second set of apertures 30 formed a spaced distance proximally from the distal end. This structure is ideally suited for use as a venous cannula during a cardiac surgical procedure.

One unique feature of the cannula assembly according to the invention is that at least a portion of the cannula body 18 is non-circular. This first non-circular portion 32 is preferably oval in cross section and is defined by a major cross-sectional axis 34 and a minor cross-sectional axis 36. As will be described further below, the incorporation of a non-circular portion 32 makes the cannula assembly according to the invention ideally suited for use in minimally invasive cardiac surgical procedures.

The obturator 16 comprises a proximal end 48 and a distal end 50. The obturator is adapted to be slidably, telescopically received inside the lumen 24 of the cannula 14. When the obturator is fully received inside the cannula lumen 24, the obturator substantially seals the second set of fluid apertures 30 so that fluid cannot enter the lumen 24 through these apertures. In addition, the obturator restricts the flow of blood through the lumen 24 which enters through the first set of fluid apertures 28.

The cannula assembly 12 described above is ideally suited for use as a venous cannula during a coronary surgical procedure similar to the cannula described in U.S. Pat. No. 4,129,129 which is expressly incorporated herein by reference. In use, the cannula 14, with the obturator 16 fully received therein, is inserted through an appropriate incision into the right atrium and the inferior vena cava. As the distal end 22 of the cannula 14 is inserted into the blood flow passing through the right atrium and inferior vena cava, blood will enter the first set of fluid apertures 28, but the obturator 16 will restrict the flow of blood through the lumen 24 and the second set of fluid apertures 30. Once the cannula 14 is properly positioned, the obturator 16 is removed from the cannula 14, and the luer connector 26 of the cannula 14 is connected to a conventional bypass system. With the cannula 14 in this position, blood enters the lumen 24 through both the first and second fluid apertures 28, 30 and is conducted to the bypass machine.

Traditional cardiac surgery is typically performed by a median sternotomy in which substantially the entire chest cavity is exposed by cutting the full length of the sternum and spreading back the sternum and ribs to expose the entire pericardium. However, a recent trend in cardiac surgery is to attempt to minimize the size of the access apertures formed in the patient's chest using techniques such as a right or left anterior thoracotomy, mini-sternotomy, and multi-port access apertures. In each of these procedures, the size of the access aperture formed in the patient's chest is considerably smaller than the traditional median sternotomy, thereby reducing the complications and possible side effects associated with such a massive wound. However, reducing the size of the access aperture raises a new set of problems not encountered in the conventional median sternotomy, namely, sufficient space for the receipt of all the instruments and equipment.

One limiting factor to reducing the size of the access aperture in any surgical procedure is the cross-sectional space requirements of the surgical tools which must be inserted through the access aperture. The cannula according to the invention is an improvement over the known cannulas because it more efficiently utilizes the limited space of the access aperture without adversely affecting the fluid flow characteristics through the cannula.

As seen in FIGS. 1–3, at least a portion 32 of the cannula body 18 is oval in cross section, and the cannula body 18 is received in an access aperture 52 formed in the chest wall 54 of the patient 56. In this example, the access aperture 52 comprises a right anterior thoracotomy. Preferably, the proximal 20 and distal 22 ends of the cannula 14 are circular in cross section while the central portion of the cannula body 18 is oval in cross section. When the oval portion 32 of the cannula is positioned in the access aperture 52, the available cross sectional area of the access aperture 52 is used more efficiently. Preferably, the cannula is positioned so that the minor cross-sectional axis 36 extends radially inwardly from the sidewall of the access aperture 52. With this structure, the cannula 14 extends a minimum distance inwardly toward the center of the access aperture 52 thereby utilizing the available space more efficiently. If a traditional cannula having a round cross section with a flow rate potential comparable to the oval-shaped cannula according to the invention were positioned in the access aperture 52, then the diameter of the round cannula would extend farther toward the center of the access aperture 52 and utilize the valuable cross-sectional area of the opening far more inefficiently.

While the preferred embodiment of the cannula 14 and cannula assembly 12 described above is a venous cannula, it is to be understood that the invention extends to any cannula inserted into the body through an access aperture including but not limited to an arterial cannula, a cardioplegia cannula (both retrograde and antigrade), a vent, a sump, or a suction tube. Similarly, FIG. 3 shows use of a cannula in a right anterior thoracotomy. It is to be understood that the benefits of the invention can be realized regardless of the particular surgical aperture which is created.

Figure 4:
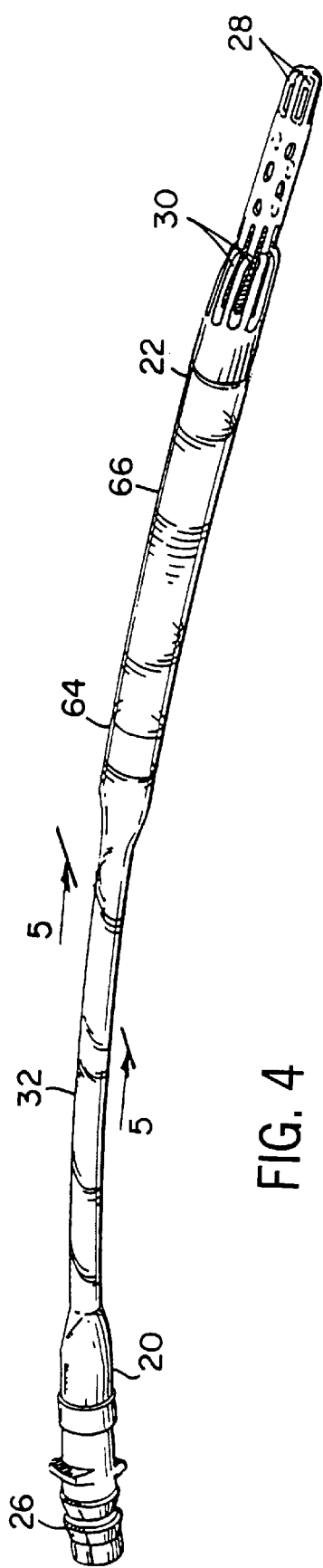
FIG. 4 is a perspective view of a second embodiment of the cannula wherein at least two portions of the cannula body are oval in cross section and the oval sections are not aligned with one another.
Figure 5:
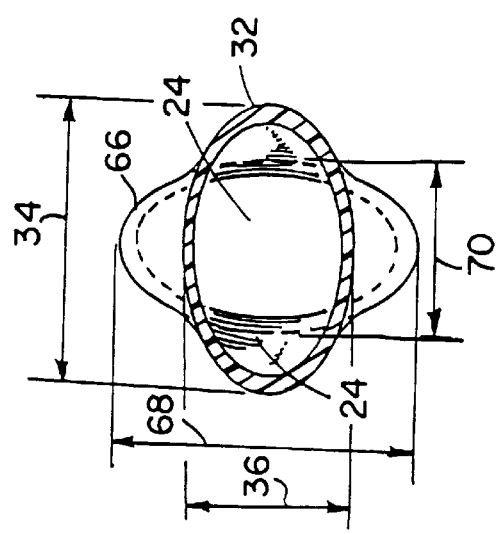
FIG. 5 is a cross section taken along lines 5—5 of FIG. 4 showing the oval cross sections of the second embodiment of the cannula body.

FIGS. 4 and 5 show a second embodiment of the cannula according to the invention. In this embodiment, the cannula 64 also includes a second non-circular portion 66. Preferably, the second non-circular portion is oval in cross section and has a major cross-sectional axis 68 and a minor cross-sectional axis 70 with the major cross-sectional axes 34, 68, respectively, of the first and second non-circular portions 32, 66 not being parallel to one another and preferably perpendicular to one another. With this structure, the first non-circular portion 32 can be positioned to extend through the access aperture 52 as described above, and the second non-circular portion 66 can be positioned either inside the body or outside the body in a particular position which requires significant bending or deflection of the cannula 64. Preferably, the second non-circular portion 66 is aligned so that the minor cross-sectional axis 70 of the second non-circular portion 66 extends radially outwardly from the arc or radius of curvature. In this orientation, the non-circular structure and the orientation of the major and minor axes with respect to the radius of curvature resists the tendency of the cannula 64 to kink or pinch closed as it is bent through the radius of curvature.

A second embodiment of the obturator 76 is shown in FIG. 6. When the cannula is used as a venous cannula during a coronary surgical operation, it is preferred to include an obturator which substantially seals the second set of fluid apertures 30 from the lumen 24 during the initial insertion of the cannula 14 into the blood flow. In the preferred embodiment of the cannula 14, the minor cross-sectional axis 36 of the non-circular portion 32 is less than the interior diameter of the distal end 22 of the cannula 14. Therefore, in order for the obturator to be telescopically inserted and removed from the lumen, whatever means are incorporated onto the obturator must be pliable or radially expandable to accommodate these diametrical constraints. In this embodiment, an expandable member such as a conventional, silicone balloon 78 is provided on the distal end 50 of the obturator 76. The obturator 76 comprises a proximal end 80 and a distal end 82. The balloon 78 is fluidly connected to an inflation lumen 84 which extends from the balloon 78, to the proximal end of the obturator. Preferably, a luer connector 86 is mounted to the terminal end of the inflation lumen 84.

The balloon is adapted for inflation from a retracted state as seen in to FIG. 6 to an expanded state which extends radially outwardly from the obturator 76 a sufficient distance to substantially seal the second set of fluid apertures 30. In use, the obturator 76 is inserted into the lumen 24 with the balloon 78 in the retracted state. Once the distal end 82 of the obturator 76 is received in the lumen 24 so that the balloon 78 is positioned immediately adjacent the second set of fluid apertures 30, the balloon 78 is inflated through the flow of pressurized fluid through the inflation lumen 84 and connector 86. The balloon 78 is inflated a sufficient amount to substantially seal the fluid apertures 30. Once the cannula assembly 12 is properly positioned in the blood flow, the balloon 78 is deflated by removing the pressurized fluid from the balloon 78 through the inflation lumen 84 and connector 86. Once the balloon 78 is sufficiently deflated, then the obturator 76 is removed from the cannula lumen 24, and the lumen is fluidly connected to the bypass system.

A third embodiment of the obturator 90 is shown in FIG. 7. Similar to the earlier embodiments, this embodiment of the obturator 90 comprises a proximal end 92 and a distal end 94. However, in this embodiment, an expandable foam member 96 is mounted on the distal end 94 of the obturator 90. In the relaxed state, the diameter of the foam member 96 is slightly larger than the interior diameter of the cannula 14 at the second set of fluid apertures 30. Therefore, when the foam member 96 is positioned immediately adjacent the apertures 30, the foam member will substantially seal the apertures 30 from the lumen 24.

In the third embodiment, the foam member 96 is formed from a soft, pliable foam which can easily be compressed by the opposed sidewalls of the cannula in the non-circular portion as the obturator 90 passes therethrough. Once the obturator 90 is fully received in the lumen 24, the foam member 96 expands outwardly a sufficient distance to substantially seal the fluid apertures 30. Similar to to the earlier embodiments, once the cannula assembly 12 is properly positioned, then the obturator is telescopically removed from the lumen. As the obturator is being pulled through the non-circular portions, the opposed sidewalls of the lumen will compress the foam member a sufficient distance to permit passage of the foam member therethrough. The foam member 96 of the third embodiment of the obturator 90 and the expandable balloon 78 of the second embodiment of the obturator 76 are only two examples of expandable means provided on the obturator to permit passage of the distal end of the obturator through the confines of the lumen and still capable of sealing the fluid apertures provided on the distal end of the catheter. It is understood that any other means which accommodate the varying diameters fall within the scope of the invention.

The preferred method for forming the cannula 14 according to the invention comprises the steps of extruding a circular length of tubing. Preferably, tubing is formed from silicone or polyvinylchloride. Depending upon the particular application, a helically wound spring may be received on the inside of the hollow tube and either be adhesively fastened therein or integrally molded therein. Next, the tubing is cut to the desired length, and then the non-circular portion is formed by positioning the length of the tube between two opposed platens and then compressing the two platens a sufficient distance to obtain the desired non-circular or oval-shaped configuration. Once the spring has been plastically deformed, it will retain the pliable cannula body in the oval or non-circular configuration. Finally, the luer connector and flow aperture member are mounted to the proximal and distal ends thereof. The cannula 14 can be compressed to create the non-circular configuration prior to or subsequent to mounting of the elements on the proximal and distal ends thereof. In the event that two different non-circular portions are formed along the length of the cannula, then the step of compressing the cannula body between two opposed platens is repeated, as necessary, for the additional non-circular sections.

With the rapid evolution of surgical procedures which minimize the size of the access aperture cut into the patient, the known, conventional, surgical tools such as cannulas, vents, sumps, or suction tubes must be adapted to accommodate such advances. The non-circular cannula according to the invention is one such modification which assists the surgeons in achieving the goal of minimizing the wound size for a variety of surgical procedures. This advantage is accomplished without adversely affecting the fluid flow rate through the tubing or otherwise adversely affecting the performance of the tubing.

Reasonable variation and modification are possible within the spirit of the foregoing specification and drawings without departing from the scope of the invention.

What is claimed is:

1. An improved cannula for use in conducting fluid to or from a body, the cannula comprising a cannula body having a proximal end, a distal end, a lumen extending between the proximal and distal ends, a fluid outlet formed on the proximal end and at least one fluid inlet formed adjacent the distal end, the improvement comprising:

a cannula body wherein the cross section of a first portion of the cannula body is non-circular and has a major cross-sectional axis and a minor cross-sectional axis, the length of the major axis being greater than the length of the minor axis and the lumen extending through said first portion of the cannula body having a cross-sectional shape the same as the cross section of the first portion of the cannula body; and a second portion of the cannula body which is non-circular, said second portion having a major cross-sectional axis and a minor cross-sectional axis, the length of the major axis being greater than the length of the minor axis, the major and minor axes of the first and second portions, respectively, being non-parallel.

2. An improved cannula according to claim 1 wherein said first portion of the cannula is oval in cross section.

3. An improved cannula according to claim 2 wherein the lumen extending through the first portion of the cannula body is oval in cross section.

4. An improved cannula according to claim 1 wherein the major axis of the first portion is parallel to the minor axis of the second portion and the minor axis of the first portion is parallel to the major axis of the second portion.

5. An improved cannula according to claim 4 wherein the first and second portions are oval in cross section.

6. An improved cannula according to claim 5 wherein the lumen extending through the first portion of the cannula body is oval in cross section and the lumen extending through the second portion of the cannula body is oval in cross section.

7. An improved cannula according to claim 1 and further comprising an obturator telescopically received in the lumen of the cannula wherein the obturator effectively seals at least a portion of the at least one fluid inlet when the obturator is fully received in the cannula lumen.

8. An improved cannula according to claim 6 wherein the obturator further comprises a proximal end, a distal end, and a radially expandable member mounted on the distal end, the expandable member being selectively expandable between a retracted state and an expanded state and when the obturator is fully received in the cannula lumen in the expanded state, the expandable member effectively seals at least a portion of the at least one fluid inlet.

9. An improved cannula according to claim 1 wherein the lumen extending through said second portion of the cannula body has a cross-sectional shape substantially similar to the cross section of the second portion of the cannula body.

10. An improved cannula according to claim 1 wherein the at least one fluid inlet comprises a first fluid inlet formed immediately adjacent the distal end and a second fluid inlet formed proximally a spaced distance from the first inlet.

11. An improved cannula according to claim 10 and further comprising an obturator telescopically received in the lumen of the cannula, the obturator being adapted to effectively, fluidly seal the second fluid inlet when the obturator is fully received in the lumen.

12. An improved cannula according to claim 10 and further comprising a luer connector mounted on the proximal end of the cannula, the luer connector being fluidly connected to the cannula lumen.

13. A method of positioning a fluid conducting cannula in a body comprising the steps of:
   providing a cannula comprising:
      a cannula body having a proximal end, a distal end, a lumen extending between the proximal and distal ends, a fluid outlet formed on the proximal end, and at least one fluid inlet formed adjacent the distal end, the cross section of a first portion of the cannula body being non-circular and having a major cross-sectional axis and a minor cross-sectional axis, the length of the major axis being greater than the length of the minor axis; and
      an obturator telescopically received in the lumen of the cannula, the obturator comprising a proximal end, a distal end and a radially expandable foam member mounted on the distal end of the obturator, the foam member being sufficiently pliable so that the foam member can be telescopically received in the cannula lumen and effectively seal at least a portion of the at least one fluid inlet when the obturator is received in the cannula lumen;
   providing a percutaneous aperture in a body;
   inserting the distal end of the cannula into the body through the percutaneous aperture; and
   positioning the cannula so that the non-circular first portion of the cannula extends through the percutaneous aperture.

14. A method according to claim 13 and further comprising the steps of:
   providing a second, non-circular portion of the cannula body, the second portion having a major cross-sectional axis and a minor cross-sectional axis, the length of the major axis being greater than the length of the minor axis, the major and minor axes of the first and second portions, respectively, being non-parallel; and
   positioning the second non-circular portion of the cannula body outside the body.

15. A method according to claim 13 and further comprising the steps of:
   providing a second, non-circular portion of the cannula body, the second portion having a major cross-sectional axis and a minor cross-sectional axis, the length of the major axis being greater than the length of the minor axis, the major and minor axes of the first and second portions, respectively, being non-parallel; and
   positioning the second non-circular portion of the cannula body inside the body.

16. A method according to claim 13 and further comprising the steps of:
   providing an obturator which is selectively, telescopically received inside the cannula lumen;
   inserting the obturator in the cannula lumen prior to inserting the cannula through the percutaneous aperture; and
   removing the obturator after the cannula has been inserted into the percutaneous aperture.

17. A method of positioning a fluid conducting cannula in a body comprising the steps of:
   providing a cannula comprising:
      a cannula body having a proximal end, a distal end, a lumen extending between the proximal and distal ends, a fluid outlet formed in the proximal end and at least one fluid inlet formed adjacent the distal end, wherein the cross section of a first portion of the cannula body is non-circular and has a major cross-sectional axis and a minor cross-sectional axis, the length of the major axis being larger than the length of the minor axis, and the lumen extending through said first portion of the cannula body having a configuration substantially similar to the cross section of the first portion of the cannula body; and
      an obturator telescopically received in the lumen of the cannula, the obturator comprising a proximal end, a distal end, and a foam member mounted on the distal end, the foam member being sufficiently pliable so that the foam member can be telescopically received in the cannula lumen and effectively seal at least a portion of the at least one fluid inlet when the obturator is fully received in the cannula lumen;
   providing a percutaneous aperture in a body;
   inserting the distal end of the cannula into the body through the percutaneous aperture; and
   positioning the cannula so that the non-circular first portion of the cannula extends through the percutaneous aperture.

* * * * *

UNITED STATES PATENT AND TRADEMARK OFFICE
CERTIFICATE OF CORRECTION

PATENT NO. : 6,146,371
DATED : Nov. 14, 2000
INVENTOR(S) : DeWindt et al.

It is certified that error appears in the above-identified patent and that said Letters Patent is hereby corrected as shown below:

At col. 7, line 23, after "minor axis", please add --and the lumen being substantially non-circular in cross-section--.

At col. 7, line 29, after "received in the", please add --non-circular--.

Signed and Sealed this

Twenty-ninth Day of May, 2001

Attest:

NICHOLAS P. GODICI

*Attesting Officer*　　　*Acting Director of the United States Patent and Trademark Office*